(12) United States Patent
Hynes et al.

(10) Patent No.: US 9,918,763 B2
(45) Date of Patent: Mar. 20, 2018

(54) BONE FIXATION ELEMENT AND METHODS OF USE

(71) Applicant: Warsaw Orthopedic, Inc., Warsaw, IN (US)

(72) Inventors: Richard A. Hynes, Melbourne Beach, FL (US); Gregory C. Marik, Collierville, TN (US); Trevor Seck, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 270 days.

(21) Appl. No.: 14/808,077

(22) Filed: Jul. 24, 2015

(65) Prior Publication Data

US 2017/0020572 A1    Jan. 26, 2017

(51) Int. Cl.
| *A61B 17/70* | (2006.01) |
| *A61B 17/86* | (2006.01) |
| *A61B 17/80* | (2006.01) |

(52) U.S. Cl.
CPC ...... *A61B 17/8605* (2013.01); *A61B 17/7032* (2013.01); *A61B 17/7035* (2013.01); *A61B 17/7044* (2013.01); *A61B 17/809* (2013.01)

(58) Field of Classification Search
CPC ............ A61B 17/7044; A61B 17/7032; A61B 17/864; A61B 17/869
See application file for complete search history.

(56) References Cited

U.S. PATENT DOCUMENTS

| 5,133,717 A * | 7/1992 | Chopin | A61B 17/7055 606/264 |
| 5,147,360 A * | 9/1992 | Dubousset | A61B 17/705 606/250 |
| 8,052,726 B2 * | 11/2011 | Nayet | A61B 17/7037 606/250 |
| 9,271,758 B2 * | 3/2016 | Marik | A61B 17/7032 |
| 9,585,697 B2 * | 3/2017 | Stachniak | A61B 17/7035 |
| 9,649,133 B2 * | 5/2017 | Strnad | A61B 17/7037 |
| 2010/0094358 A1 * | 4/2010 | Moore | A61B 17/0642 606/319 |
| 2011/0098747 A1 * | 4/2011 | Donner | A61B 17/70 606/264 |
| 2011/0184470 A1 * | 7/2011 | Gorek | A61B 17/7011 606/279 |
| 2011/0230884 A1 * | 9/2011 | Mantzaris | A61B 17/1717 606/64 |
| 2011/0230920 A1 * | 9/2011 | Gorek | A61B 17/7001 606/305 |
| 2011/0282398 A1 * | 11/2011 | Overes | A61B 17/861 606/304 |
| 2013/0085534 A1 * | 4/2013 | Hainard | A61B 17/7055 606/278 |

(Continued)

*Primary Examiner* — Jacqueline Johanas (57) ABSTRACT

A bone fixation element includes a distal end defining a longitudinal axis and being configured to penetrate tissue, a proximal end defining an axial opening disposed in communication with a transverse passageway and a fastener including a proximal portion having spaced apart walls that define an implant cavity and a distal portion disposed with the transverse passageway and configured to penetrate tissue. The distal end is disposable in spaced apart relation to the distal portion of the fastener within tissue. Methods of use are disclosed.

20 Claims, 5 Drawing Sheets

(56) References Cited

U.S. PATENT DOCUMENTS

| | | | |
|---|---|---|---|
| 2014/0018858 A1* | 1/2014 | Laeng | A61B 17/7002 606/270 |
| 2014/0058457 A1* | 2/2014 | Appenzeller | A61B 17/864 606/304 |
| 2014/0066991 A1* | 3/2014 | Marik | A61B 17/7032 606/279 |
| 2014/0094858 A1* | 4/2014 | Picetti | A61B 17/7001 606/308 |
| 2014/0200618 A1* | 7/2014 | Donner | A61B 17/1757 606/281 |
| 2014/0249581 A1* | 9/2014 | Stachniak | A61B 17/7035 606/264 |
| 2014/0257410 A1* | 9/2014 | Biedermann | A61B 17/7037 606/304 |
| 2015/0032159 A1* | 1/2015 | Beger | A61B 17/8605 606/265 |
| 2015/0134014 A1* | 5/2015 | Palmer | A61B 17/863 606/304 |
| 2015/0223847 A1* | 8/2015 | Trieu | A61B 17/683 606/246 |
| 2016/0095630 A1* | 4/2016 | Powers | A61B 17/7022 606/279 |
| 2016/0106477 A1* | 4/2016 | Hynes | A61B 17/7044 606/279 |
| 2016/0106479 A1* | 4/2016 | Hynes | A61B 17/7059 606/286 |
| 2016/0143667 A1* | 5/2016 | Beger | A61B 17/7032 606/272 |

* cited by examiner

BONE FIXATION ELEMENT AND METHODS OF USE

TECHNICAL FIELD

The present disclosure generally relates to medical devices for the treatment of spinal disorders, and more particularly to a spinal implant system including a bone fixation element that provides stabilization while reducing stress on spinal elements.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support the vertebral members. During surgical treatment, one or more rods and bone fasteners can be delivered to a surgical site. The rods may be attached via the fasteners to the exterior of two or more vertebral members. This disclosure describes an improvement over these prior art technologies.

SUMMARY

In one embodiment, in accordance with the principles of the present disclosure, a bone fixation element is provided. The bone fixation element includes a distal end defining a longitudinal axis. The distal end is configured to penetrate tissue. A proximal end defines an axial opening disposed in communication with a transverse passageway. A fastener includes a proximal portion having spaced apart walls that define an implant cavity and a distal portion disposed with the transverse passageway and configured to penetrate tissue. The distal end is disposable in spaced apart relation to the distal portion of the fastener within tissue.

In one embodiment, in accordance with the principles of the present disclosure, a method for treating a vertebral column is provided. The method includes the steps of: providing a bone fixation element comprising a distal end defining a longitudinal axis, a proximal end defining an axial opening disposed in communication with a transverse passageway, and a fastener having a proximal portion including spaced apart walls that define an implant cavity and a distal portion disposed with the transverse passageway; connecting the distal end with tissue; rotating the distal portion relative to the proximal end for alignment with the transverse passageway and passage through the axial opening; and disposing the distal portion through the axial opening to connect the distal portion with tissue such that the distal end is disposed in spaced apart relation to the distal portion of the fastener.

In one embodiment, the bone fixation element includes a fastener including a proximal portion having spaced apart walls that define an implant cavity and a distal portion configured to penetrate tissue. The distal portion includes a threaded first portion, a smooth intermediate portion and a second portion. A distal end defines a longitudinal axis and is configured to penetrate tissue. A proximal end includes an inner threaded surface and a plate that defines an axial opening disposed in communication with a transverse passageway configured to guide the distal portion of the fastener into tissue along a selected trajectory. The transverse passageway defines a first axis disposed at an angular orientation of 30 degrees relative to the longitudinal axis. The inner threaded surface is configured for engagement with the first portion of the fastener. The plate has a first surface configured to engage tissue and a planar second surface disposed adjacent the proximal portion of the fastener. The first surface includes a plurality of spikes extending therefrom disposed radially about the first surface. The distal portion of the fastener is disposed with the transverse passageway and is configured to penetrate tissue. The distal portion of the fastener is rotatable through 360° in a plurality of planes for alignment with the transverse passageway and passage through the axial opening such that the distal end is disposable in spaced apart relation to the distal portion of the fastener within tissue.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

The exemplary embodiments of a surgical system, a bone fixation element and related methods of use disclosed are discussed in terms of medical devices for the treatment of musculoskeletal disorders and more particularly, in terms of a spinal implant system including a bone fixation element and a method for treating a vertebral column. In one embodiment, a first portion of the bone fixation element is engageable with tissue in a medial orientation and a second portion of the bone fixation element is engageable with tissue in a lateral orientation. It is envisioned that the portions of the bone fixation element and the fastener of the bone fixation element may alternate trajectories such that the first portion is inserted into tissue in a lateral orientation and the second portion is inserted into bone or other tissue in a medial orientation.

In one embodiment, the system includes a bone fixation element having a distal end that is threaded. In one embodiment, the distal end has a smooth or even surface. In one embodiment, the bone fixation element includes a plate having spikes extending therefrom. In one embodiment, the bone fixation element includes a plate without spikes extending therefrom and a cortical thread extending around a proximal end of the bone fixation element such that the bone fixation element can be threaded to fully seat within tissue after impaction of the bone fixation element with tissue. In one embodiment, an outer diameter of a proximal end of the bone fixation element is 8.5 millimeters (mm).

In one embodiment, the system includes a bone fixation element having a fastener with proximal threads, which increase the diameter of a sleeve of the bone fixation element. It is envisioned that the proximal threads will have minimal cortical purchase at an exit point of the fastener. It is further envisioned that the proximal threads may be smooth to interface with a distal end of the bone fixation element.

In one embodiment, the system includes a fastener including a smooth outer surface configured to prevent toggle of the bone fixation element with tissue, such as, for example, bone. It is envisioned that the smooth outer surface may extend the entire length or over only a portion of the fastener. It is further envisioned that the length of the fastener can vary.

In one embodiment, the system includes a bone fixation element having a distal end including a smooth outer surface configured to prevent toggle of the bone fixation element with tissue, such as, for example, bone. It is envisioned that the smooth outer surface may extend the entire length or over only a portion of the distal end. It is contemplated that the length of the distal end may vary. It is further contemplated that the length of cortical threads on a distal end portion of a fastener of the bone fixation element may vary. In one embodiment, the distal portion of the fastener captures cortical bone. It is envisioned that the distal portion of the bone fastener includes cortical threads that extend the entire length of the fastener. In one embodiment, the length of the cortical threads of the distal portion is greater than the length of cortical threads on a distal end of the bone fixation element.

In one embodiment, the system includes a bone fixation element having an inner surface defining a passageway configured to guide a fastener. It is envisioned that the passageway may provide a fastener interface.

In one embodiment, the system includes a bone fixation element having a fastener disposed at a 30 degree angle relative to a distal end of the bone fixation element. In one embodiment, the fastener is disposed at a 15 degree angle relative to the distal end of the bone fixation element. In one embodiment, the fastener is disposed at 5 degree increments relative to the distal end of the bone fixation element. In one embodiment, the fastener has a sacral iliac trajectory.

In one embodiment, the system includes a bone fixation element having a plate disposed at an angle relative to a distal end of the bone fixation element. It is contemplated that the angle between the plate and the distal end provides a dorsal surface contact with the sacrum when the plate engages the sacrum. In one embodiment, the angle between the plate and the distal end is acute. In one embodiment, the distal end of the bone fixation element is solid. In one embodiment, the distal end of the bone fixation element has a cage geometry configured for graft and/or tissue placement.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, rumor and fractures. It is contemplated that the present disclosure may be employed with other osteal and bone related applications, including those associated with diagnostics and therapeutics. It is further contemplated that the disclosed bone fixation element and methods of use may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic, sacral and pelvic regions of a spinal column. The system and methods of use of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system including a bone fixation element, related components and methods of employing the surgical system including the bone fixation element in accordance with the principles of the present disclosure. Alternate embodiments are also disclosed. Reference will now be made in detail to the exemplary embodiments of the present disclosure, which are illustrated in the accompanying figures. Turning now to FIGS. 1-4, there is illustrated components of a surgical system including a bone fixation element 30 in accordance with the principles of the present disclosure.

The components of the surgical system can be fabricated from biologically acceptable materials suitable for medical applications, including metals, synthetic polymers, ceramics and bone material and/or their composites, depending on the particular application and/or preference of a medical practitioner. For example, the components of the surgical system, individually or collectively, can be fabricated from materials such as stainless steel alloys, commercially pure titanium, titanium alloys, Grade 5 titanium, super-elastic titanium alloys, cobalt-chrome alloys, stainless steel alloys, super-elastic metallic alloys (e.g., Nitinol, super elasto-plastic metals, such as GUM METAL® manufactured by Toyota Material incorporated of Japan), ceramics and composites thereof such as calcium phosphate (e.g., SKELITE™ manufactured by Biologix inc.), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of the surgical system may have material composites, including the above materials, to achieve various desired characteristics such as strength, rigidity, elasticity, compliance, biomechanical performance, durability and radioiucency or imaging preference. The components of the surgical system, individually or collectively, may also be fabricated from a heterogeneous material such as a combination of two or more of the above-described materials. The components of the surgical system may be monolithically formed, integrally connected or include fastening elements and/or components, as described herein.

Element 30 includes a fastener 32 having a proximal portion 34 including spaced apart walls 36, 38 that define an implant cavity 40 therebetween. Cavity 40 is configured for disposal of a spinal construct, such as, for example a vertebral rod, with fastener 32. Cavity 40 has a substantially U-shaped cross-sectional configuration for disposal of the rod. It is envisioned that all or only a portion of cavity 40 may be variously configured and dimensioned, such as, for example, planar, concave, convex, polygonal, irregular, uniform, non-uniform, staggered, tapered, consistent or variable, depending on the requirements of a particular application. It is further envisioned that walls 36, 38 may each include a threaded inner surface configured to engage a retaining element such as, for example, a set screw to maintain an implant in cavity 40.

Fastener 32 includes a distal portion 42 configured to penetrate tissue, such as, for example, bone. Portion 42 includes a first portion 44 including an outer surface having an external thread form, a smooth intermediate portion 46 and a second portion 48. The thread form on the outer surface of portion 44 is configured to penetrate tissue, such as, for example, bone to fix fastener 32 in such tissue. In one embodiment, the thread form on the outer surface of portion 44 is configured to fix fastener 32 into cortical bone, such as, for example, cortical bone in an ala of a sacrum. It is contemplated that the thread form on the outer surface of portion 44 may extend the entire length of portion 42 or may extend only part of the length of portion 42. It is envisioned that portion 44 may have an outer surface, which is free of threads and/or other engaging structures, such that the outer surface of portion 44 is smooth and/or even. It is contemplated that the outer surface of portion 44 may have various cross-sectional configurations, such as, for example, square, triangular, trapezoidal or polygonal, depending upon the requirements of a particular application. It is further contemplated that all or only a portion of portion 42 may have various surface configurations, such as, for example, rough, threaded, arcuate, undulating, porous, semi-porous, dimpled, polished and/or textured according to the requirements of a particular application.

In one embodiment, portion 46 has a smooth outer surface so as to prevent fastener 32 from toggling during implantation and/or assembly, for example, when fastener 32 is engaged with another portion of element 30.

Figure 4:
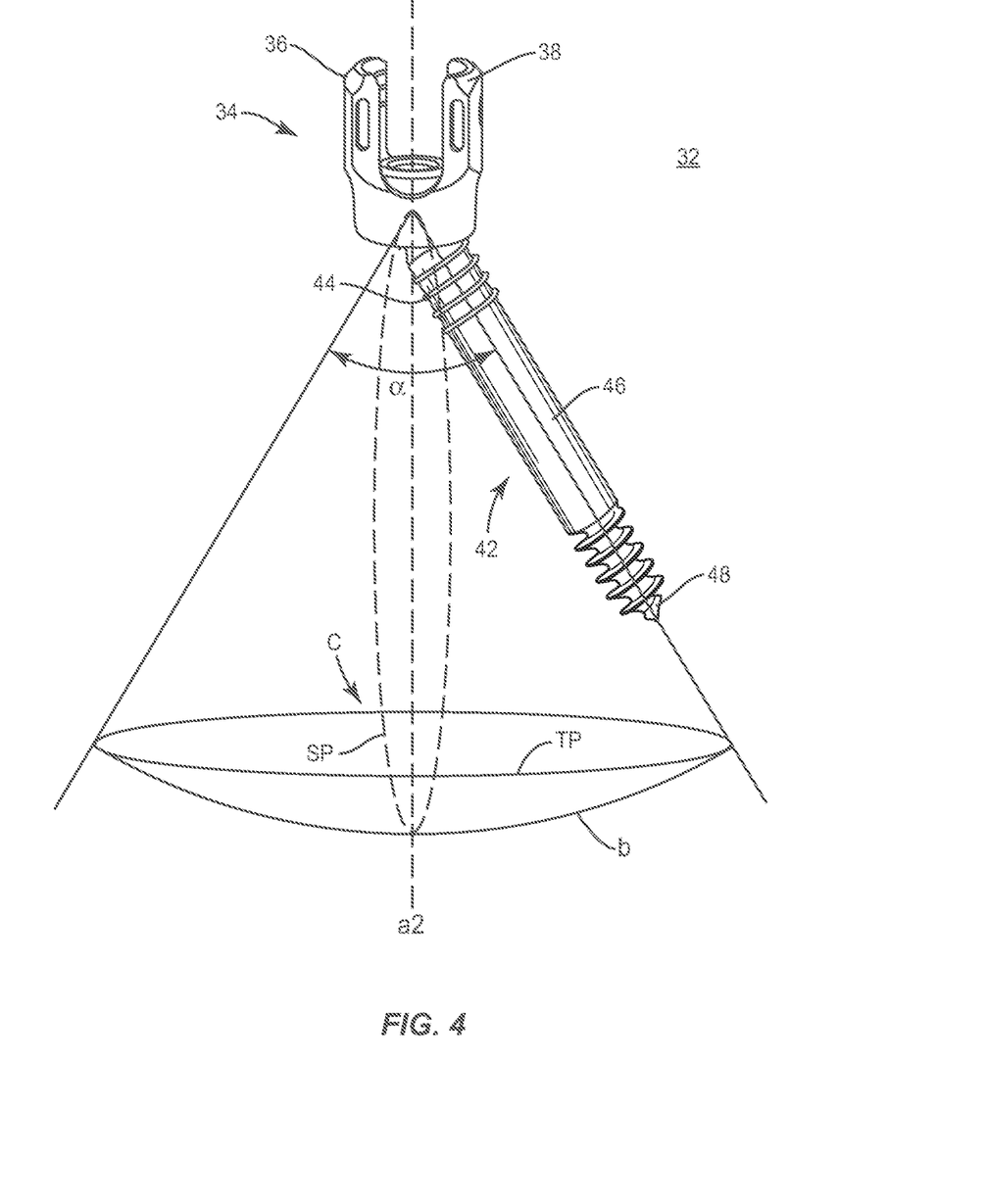
FIG. 4 is a perspective view of a component of the bone fixation element shown in FIG. 1.

Portion 42 is rotatable relative to portion 34 through an angular range of 0-360 degrees in a plurality of planes, such as, for example, the sagittal, coronal or transverse plane of a body of a patient for alignment with another portion of element 30, as will be discussed. Portion 42 is rotatable to a selected angle through and within angular range a relative to a second axis a2 in a plurality of planes that lie in a cone configuration C, as shown in FIG. 4. The area and/or volume defined by cone C, which includes the configuration disposed between axis a2 and a circular base b, is defined by the range of motion of portion 42 about axis a2. The plurality of planes includes a locus of all straight line segments that join axis a2 and base b. For example, portion 42 is separately rotatable to a selected angle within angular range a in each plane corresponding to a particular straight line segment that lies in cone configuration C. It is contemplated that portion 42 may rotatable through the individual diameters, chords, section and/or radii of base b and/or other portions of cone C. In one embodiment, portion 42 is rotatable to a selected angle within angular range a in a sagittal plane of a body of a patient, corresponding to a particular plane that lies in cone C. In one embodiment, portion 42 is rotatable to a selected angle within angular range a in a transverse plane of the body, corresponding to a particular plane that lies in cone C. In one embodiment, portion 42 is rotatable to a selected angle within angular range a in a coronal plane of the body, corresponding to a particular plane that lies in cone C.

Portion 42 has a cylindrical cross section configuration that is consistent between portion 44 and portion 46 such that portion 42 has a uniform diameter between portion 44 and portion 46. Portion 42 is tapered between portion 46 and portion 48 such that portion 46 has a diameter, which is greater than that of portion 48. It is envisioned that all or only a portion of portion 42 may have alternate cross section configurations, such as, for example, oval, oblong, triangular, square, polygonal, irregular, uniform, non-uniform, offset, staggered, undulating, arcuate, variable and/or tapered.

Portion 48 includes an outer surface having an external thread form configured to fix fastener 32 with tissue, such as, for example, bone. The thread form on portion 48 is different from the thread form on portion 42. The thread form of portion 48 is configured to engage fastener 32 with a portion of element 30. For example, portion 48 may include fine threads for fixation with bone and portion 44 may include course threads for fixation with a portion of element 30. It is contemplated that the thread form on the outer surface of portion 42 and/or portion 48 may include a single thread turn or a plurality of discrete threads. It is further contemplated that other engaging structures may be located on portion 42 and/or portion 48, such as, for example, a nail configuration, barbs, expanding elements, raised elements and/or spikes to facilitate engagement of portion 42 and/or portion 48 with tissue and/or another portion of element 30. It is envisioned that the outer surface of portion 42 may include one or a plurality of openings. It is further envisioned that all or only a portion of portion 42 may be cannulated.

Element 30 includes a distal end 50. Distal end 50 defines a longitudinal axis a and has a substantially cylindrical cross section configuration. A first end 52 of end 50 has outer surface including an external thread form configured to penetrate tissue, such as, for example, bone. It is contemplated that a length of the thread form on the outer surface of portion 48 may be greater than a length of the thread form on the outer surface of end 52. In one embodiment, the outer surface of end 52 is free of threads and/or other engaging structures. It is envisioned that the thread form on the outer surface of end 52 may include a single thread turn or a plurality of discrete threads. It is further envisioned that other engaging structures may be located on end 52, such as, for example, a nail configuration, barbs, expanding elements, raised elements and/or spikes to facilitate engagement of end 50 with tissue. It is contemplated that all or only a portion of end 50 may have alternate cross section configurations, such as, for example, oval, oblong, triangular, square, polygonal, irregular, uniform, non-uniform, offset, staggered, undulating, arcuate, variable and/or tapered. In one embodiment, end 50 has a solid configuration. It is contemplated that end 50 may be variously configured, and may include a configuration such as, for example, solid or hollow.

Figure 1:
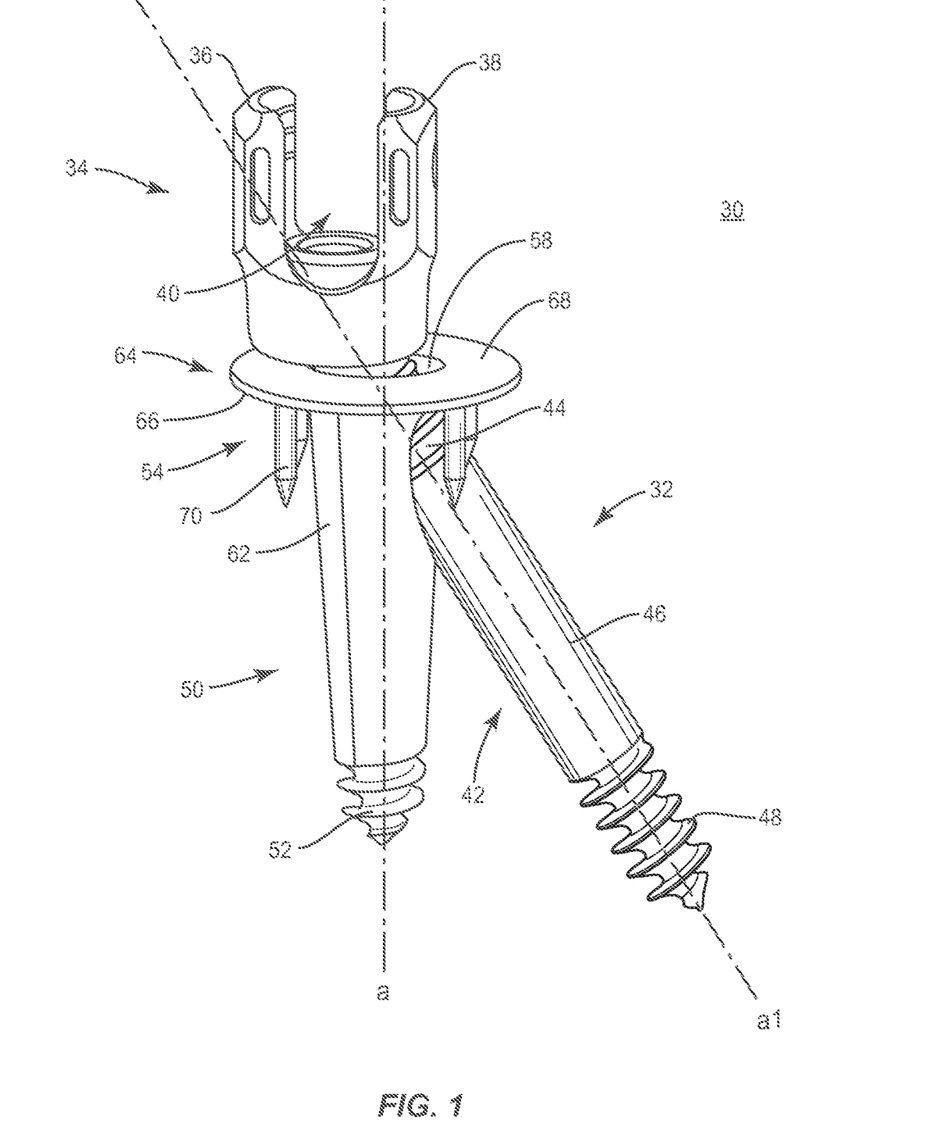
FIG. 1 is a perspective view of one particular embodiment of a surgical system including a bone fixation element in accordance with the principles of the present disclosure.
Figure 2:
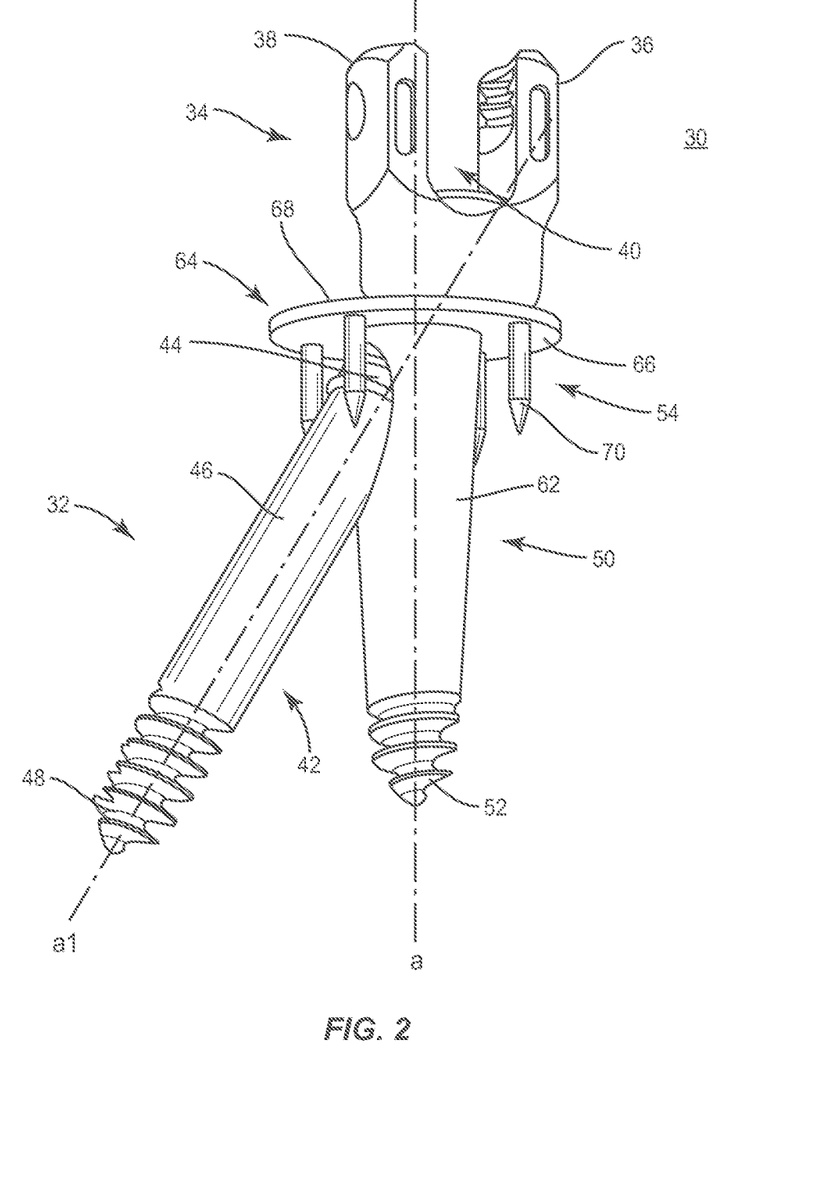
FIG. 2 is a perspective view of the bone fixation element shown in FIG. 1.
Figure 3:
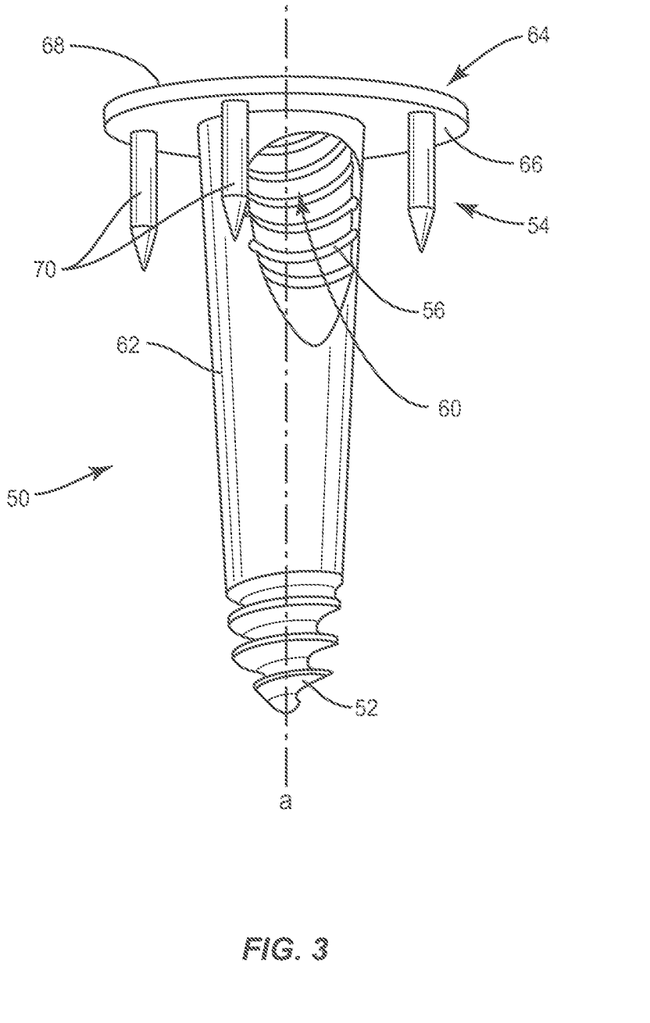
FIG. 3 is a perspective view of a component of the bone fixation element shown in FIG. 1.

Walls 36, 38 each extend parallel to axis a. Portion 34 is offset from axis a when fastener 32 is engaged with end 50, as shown in FIGS. 1 and 2, such that cavity 40 is also offset from axis a. Portion 34 is biased to a side of end 50 opposite a side of end 50 through which passageway 60 extends. It is envisioned that portion 34 may also be aligned with axis a when fastener 32 is engaged with end 50 such that cavity 40 is also aligned with axis a.

Element 30 includes a proximal end 54. Proximal end 54 includes an inner threaded surface 56 defining an axial opening 58 disposed in communication with a transverse passageway 60. In one embodiment, passageway 60 is configured to guide portion 42 into tissue along a selected trajectory.

Passageway 60 extends from opening 58 through a side surface 62 of end 50. Side surface 62 is even or smooth so as to prevent end 50 from toggling when end 50 is engaged with tissue, such as, for example, bone. Passageway 60 defines a first axis a1 disposed at an angular orientation of 30 degrees relative to axis a. In one embodiment, axis a1 is disposed at an angle of 30 degrees relative to axis a. The thread form on surface 56 is configured to engage the thread form on the outer surface of portion 44. Passageway 60 has a substantially cylindrical cross sectional configuration and a width or diameter which is uniform. It is contemplated that all or only a portion of opening 58 may be variously configured and dimensioned, such as, for example, circular, oval, oblong, triangular, square, rectangular, polygonal, irregular, uniform, non-uniform, offset, staggered, tapered, consistent or variable, depending on the requirements of a particular application. It is envisioned that all or only a portion of end 50 may have alternate cross section configurations, such as, for example, oval, oblong, triangular, square, polygonal, irregular, uniform, non-uniform, offset, staggered, undulating, arcuate, variable and/or tapered. It is further envisioned that passageway 60 and/or axis a1 may be disposed at alternate orientations relative to longitudinal axis a, such as, for example, transverse, perpendicular and/or other angular orientations such as acute or obtuse and/or may be offset or staggered and/or may be disposed at alternative angular orientations relative to axis a, depending on the requirements of a particular application.

In one embodiment, passageway 60 is disposed along a sacroiliac trajectory such that at least a portion of fastener 32 engages a sacroiliac joint of a patient, or an area adjacent a sacroiliac joint of a patient when fastener 32 is disposed with passageway 60. It is further contemplated that passageway 60 may be disposed in other trajectories, such as, for example, anterior, posterior, medial, cephalad/caudal, lateral and/or those described herein.

Surface 56 is configured for engagement with portion 44 to maintain portion 42 in the selected trajectory. In one embodiment, the threaded portion of portion 44 may have an axial length, which is greater than that of passageway 60 such that at least a portion of the thread on portion 44 extends beyond passageway 60 when fastener 32 is disposed in passageway 60 to allow for cortical purchase at an interface where fastener exits passageway 60. In one embodiment, the threaded portion of portion 44 may have a length that is less than or equal to a length of passageway 60 such that the threaded portion of portion 44 is disposed within passageway 60 when fastener 32 is disposed in passageway 60.

End 54 has a width or diameter, which is greater than that of end 52 such that element 30 is tapered between end 54 and end 52. In one embodiment, end 54 has an outer diameter, which is approximately 8.5 mm. It is envisioned that element 30 may be variously configured and dimensioned between end 54 and end 50, such as, for example, planar, concave, convex, polygonal, irregular, uniform, non-uniform, staggered, tapered, consistent or variable, depending on the requirements of a particular application. In one embodiment, end 54 includes an outer surface having a thread form about a circumference thereof, such as, for example, a cortical thread configured to engage tissue, such as, for example, bone, such that element 30 can fully seat in the tissue after impaction.

End 54 includes a plate 64 that defines opening 58. Plate 64 is substantially circular and has a first planar surface 66 configured to engage tissue and a planar second surface 68 engaging portion 34. Surface 66 includes at least one bone penetrating element extending therefrom, such as, for example, a spike 70. Surface 66 includes a plurality of spikes 70 extending therefrom and disposed radially about surface 66 in a circumferential orientation. It is contemplated that other engaging structures and/or bone penetrating elements may be located on surface 66, such as, for example, a nail configuration, barbs, expanding elements and/or raised elements to facilitate engagement of plate 64 with tissue, such as, for example, bone. It is further contemplated that the engaging structures and/or bone penetrating elements on surface 66 may be variously configured, such as, for example, uniform, non-uniform, or staggered, depending on the requirements of a particular application. It is envisioned that all or only a portion of plate 64 may be variously configured and dimensioned, such as, for example, circular, oval, oblong, triangular, square, rectangular, polygonal, or irregular, depending on the requirements of a particular application.

Plate 64 has a height between surfaces 66, 68, which is substantially uniform such that plate 64 has a disc shaped configuration. It is contemplated that the height of plate 64 between surfaces 66, 68 may vary such that the height of one side of plate 64 is different than the height of another side of plate 64 such that plate has a wedge shaped configuration. In one embodiment, plate 64 is disposed at an acute angular orientation relative to axis a to maximize surface contact with tissue such as, for example, bone. It is envisioned that plate may be disposed through angular ranges in various orientations relative to axis a, such as, for example, transverse, perpendicular and/or other angular orientations such as acute or obtuse, and/or may be offset or staggered.

Figure 5:
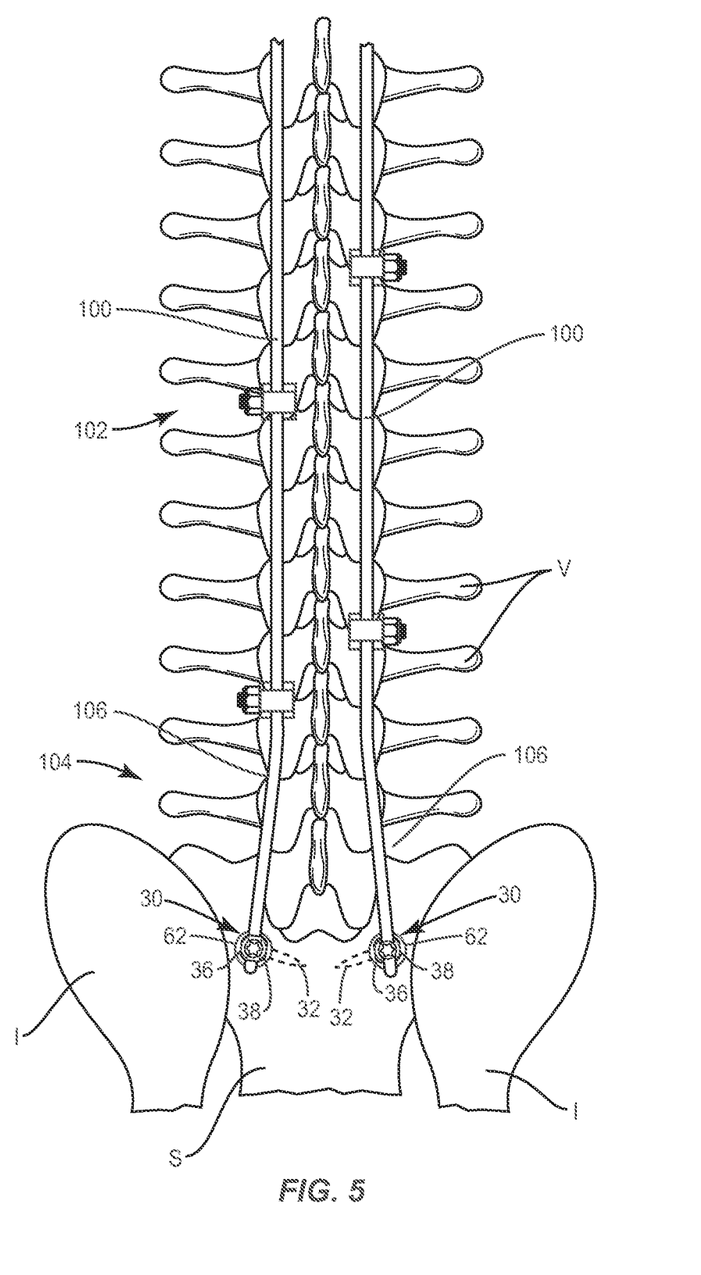
FIG. 5 is a plan view of one embodiment of a surgical system in accordance with the principles of the present disclosure disposed with vertebrae.

In assembly, operation and use, a surgical system including bone fixation element 30, similar to that described above, is employed with a surgical procedure for treatment of a spinal disorder affecting a section of a spine of a patient, as discussed herein. In particular, the surgical system, including element 30, is employed with a surgical procedure for treatment of a condition or injury of an affected section of the spine including vertebrae V, as shown in FIG. 5. In one embodiment, the system including element 30 is attached to vertebrae V for a surgical arthrodesis procedure, such as a fusion of the affected section of the spine, such as, for example, the sacroiliac joint, to facilitate healing and therapeutic treatment. In one embodiment, the system including element 30 is attached to vertebrae V for a dynamic stabilization application.

In use, to treat the affected section of the spine, a medical practitioner obtains access to a surgical site including vertebrae V in any appropriate manner, such as through incision and retraction of tissues. It is envisioned that the components of the surgical system may be used in any existing surgical method or technique including open surgery, mini-open surgery, minimally invasive surgery including percutaneous surgical implantation, whereby vertebrae V is accessed through a micro-incision, or sleeve that provides a protected passageway to the area. Once access to the surgical site is obtained, the particular surgical procedure is performed for treating the spinal disorder. The components of the surgical system, including element 30 are employed to augment the surgical treatment. Element 30 and a spinal implant, such as, for example, a vertebral rod 100 can be delivered or implanted as a pre-assembled device or can be assembled in situ. The surgical system may be may be completely or partially revised, removed or replaced.

The surgical system of the present disclosure extends from a section 102 to a section 104 disposed adjacent a sacroiliac region (SIR) of the patient. Section 104 includes two axially aligned and spaced apart rods 100 that extend to section 102. Rods 100 each have a rigid, arcuate portion 106 extending across a sacrum S of region SIR. A first element 30 and a second element 30 are configured for fixation with spaced apart regions of sacrum S.

Pilot holes are made in the regions of sacrum S corresponding to each receiving end 50. Portions 52 are inserted or otherwise connected to the regions of sacrum S according to the particular requirements of the surgical treatment. Ends 50 are advanced distally along axis a into sacrum S until plates 64 engage the surfaces of sacrum S. Surfaces 66 include bone penetrating elements extending therefrom. The bone penetrating elements are driven for fixation into the surfaces of sacrum S. Outer surfaces of ends 52 and/or ends 54 include a thread form. Elements 30 are rotated in a first direction, such as, for example, a clockwise direction, such that the thread forms on the outer surfaces of ends 52 and/or ends 54 engage the surfaces of sacrum S to thread ends 50 for fixation with sacrum S. It is envisioned that ends 50 may be advanced into sacrum S until plates 64 are flush with the surfaces of sacrum S.

Additional pilot holes, disposed adjacent the pilot holes made for ends 50, are made in sacrum S for receiving fasteners 32. The pilot holes for fasteners 32 are made by inserting an instrument, such as, for example, a drill, through passageways 60 of ends 50 and forming the pilot holes in tissue adjacent to distal ends of passageways 60 such that the pilot holes for fasteners 32 are aligned with axis a1.

Portion 42 is rotated to a selected angle through and within angular range a about axis a2 in a plurality of planes, as described with regard to FIG. 4. Portion 42 is rotated relative to end 54 such that portion 42 is parallel with axis a1. Fastener 32 is then positioned such that portion 42 is aligned with passageway 60.

Portion 48 is inserted into opening 58. Fastener 32 is advanced along axis a1 through passageway 60 such that the thread form on the outer surface of portion 44 is aligned with the thread form on surface 56. To engage fastener 32 with end 50, fastener 32 may be rotated in a first direction, such as, for example, a clockwise direction, relative to end 50 such that the thread form on the outer surface of portion 44 engages the thread form on surface 56 to maintain fastener 32 in passageway 60 such that fastener 32 is disposed at a trajectory defined by the trajectory of passageway 60. Portion 42 is selectively and freely rotatable relative to portion 34.

With ends 50 connected to sacrum S, each portion 42 is rotated relative to end 50 such that each portion 42 is coaxial to a respective axis at Each fastener 32 is positioned in alignment with a respective passageway 60. Passageway 60 guides fastener 32 into engagement with sacrum S. Portions 48 are inserted into openings 58 and fasteners 32 are advanced along axis a1 through passageways 60 such that the thread forms on the outer surface of portions 44 are aligned with the thread forms on surfaces 56. Fasteners 32 may be rotated in the first direction such that the thread forms on the outer surface of portions 44 engage the thread forms on surfaces 56 to maintain fasteners 32 in passageways 60 such that fasteners 32 are disposed with ends 50 at a trajectory defined by the trajectory of passageways 60. As fasteners 32 are rotated in the first direction, the thread form on the outer surfaces of portions 48 engage surfaces of sacrum S to fix fasteners 32 with sacrum S. Portion 42 and end 50 are disposed in spaced apart relation when fastener 32 and end 50 are fixed in sacrum S.

Portion 34 is selectively and freely rotatable relative to portion 42 and/or end 50 such that portion 106 of each rod 100 may be moved within cavity 40 of each element 30 by sliding portion 106 within cavity 40. According to the orientation and position of sections 102, 104 of each rod 100, elements 30 are independently and selectively positioned such that each cavity 40 is selectively rotatable relative to portion 42 and/or end 50. Cavity 40 is relatively rotatable to receive, engage and accommodate the orientation and position of portions 106. This configuration allows orientation of each cavity 40 to receive each of portions 106 such that portions 32 can capture rods 100.

Coupling elements, such as, for example, setscrews may be torqued and threaded with each portion 34 to securely attach rods 100 with sacrum S. Each setscrew may be threaded into a threaded portion of an inner surface of walls 36, 38 such that the setscrew engages rod 100. As the setscrew is threaded into walls 36, 38, the setscrew applies a force to rod 100 disposed with implant cavity 40. This force is transmitted through rod 100 such that rod 100 engages the surfaces that define cavity 40 causing at least a portion of portion 34 to engage plate 64. This configuration fixes element 30 in an orientation to prevent portion 34 from moving relative to portion 42 and/or end 50 such that element 30 may receive and accommodate the orientation and position of sections 102, 104. In one embodiment, upon completion of the procedure, the surgical instruments and non-implant components of the surgical system are removed from the surgical site and the incision is closed. In one embodiment, elements 30 may be attached to surfaces of ilium I, similar to the method described above with regard to sacrum S.

Element 30 may be employed as a bone screw, pedicle screw, mono-axial screw or multi-axial screw used in spinal surgery. It is contemplated that the components of the surgical system including all or only a portion of element 30 may be coated with an osteoconductive material such as hydroxyapatite and/or osteoinductive agent such as a bone morphogenic protein for enhanced bony fixation. It is further contemplated that components of the surgical system including all or a portion of element 30 may be coated with therapeutic and/or pharmacological agents for release, including sustained release, to treat, for example, pain, inflammation and degeneration. Element 30 can be made of radiolucent materials such as polymers. Radiomarkers may be included for identification under x-ray, fluoroscopy, CT, or other imaging techniques. Metallic or ceramic radiomarkers, such as tantalum beads, tantalum pins, titanium pins, titanium endcaps, and platinum wires can be used.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A bone fixation element comprising:
   a distal end comprising a shaft defining a longitudinal axis, the shaft comprising a proximal end having an axial opening and a threaded end configured to penetrate tissue, the shaft comprising a transverse passageway that extends through a side surface of the shaft; and
   a fastener including a proximal portion having spaced apart walls that define an implant cavity and a distal portion that extends through the axial opening and the transverse passageway such that the proximal portion sits above the proximal end of the shaft, the distal portion being configured to penetrate tissue,
   wherein the distal end is disposable in spaced apart relation to the distal portion of the fastener within tissue.

2. A bone fixation element as recited in claim 1, wherein the transverse passageway defines a first axis disposed at an angular orientation relative to the longitudinal axis.

3. A bone fixation element as recited in claim 1, wherein the transverse passageway defines a first axis disposed at an angular orientation of 30 degrees relative to the longitudinal axis.

4. A bone fixation element as recited in claim 1, wherein the proximal end includes a plate that defines the axial opening, the plate having a first surface configured to engage tissue and a second surface engaging the proximal portion.

5. A bone fixation element as recited in claim 1, wherein the proximal end includes a plate disposed at an angular orientation relative In the longitudinal axis, the plate having a first surface configured to engage tissue and a second surface engaging the proximal portion.

6. A bone fixation element as recited in claim 1, wherein the transverse passageway is disposed along a sacral iliac trajectory.

7. A bone fixation element as recited in claim 1, wherein the proximal end includes a plate that defines the axial opening, the plate having a first surface configured to engage tissue and a second surface engaging the proximal portion, the first surface including at least one bone penetrating element extending therefrom.

8. A bone fixation element as recited in claim 1, wherein the proximal end includes a plate that defines the axial opening, the plate having a first surface configured to engage tissue and a second surface engaging the proximal portion, the first surface including a plurality of spikes extending therefrom.

9. A bone fixation element as recited in claim 1, wherein the proximal end includes a plate that defines the axial opening, the plate having a first surface configured to engage tissue and a second surface engaging the proximal portion, the first surface including a plurality of spikes extending therefrom and being disposed radially about the first surface.

10. A bone fixation element as recited in claim 1, wherein the proximal end includes a plate that defines the axial opening, the plate having a first surface configured to engage tissue and a second surface engaging the proximal portion, the first surface including a plurality of spaced apart spikes disposed in a circumferential orientation about the plate.

11. A bone fixation element as recited in claim 1, wherein the proximal end includes an inner threaded surface that defines the transverse passageway, the distal portion includes a first portion, an intermediate portion and a second portion, the first portion of the distal portion being threaded for engagement with the inner threaded surface.

12. A bone fixation element as recited in claim 1, wherein the distal portion includes a first portion, an intermediate portion and a second portion, the intermediate portion being smooth to engage tissue in an anti-toggle configuration.

13. A bone fixation element as recited in claim 1, wherein the transverse passageway is configured to guide the distal portion into tissue along a selected trajectory.

14. A bone fixation element as recited in claim 1, wherein a portion of the distal end has a solid configuration.

15. A bone fixation element as recited in claim 1, wherein the distal portion is rotatable through 360° in a plurality of planes for alignment with the transverse passageway and passage through the axial opening.

16. A bone fixation element as recited in claim 1, wherein the longitudinal axis is straight and the axial opening and the threaded end are coaxial with the longitudinal axis, the transverse passageway extending at an acute angle relative to the longitudinal axis.

17. A method for treating a vertebral column, the method comprising the steps of:
   providing a bone fixation element comprising:
      a distal end comprising a shaft defining a longitudinal axis, the shaft comprising a proximal end having an axial opening and a threaded end configured to penetrate tissue, the shaft comprising a transverse passageway that extends through a side surface of the shaft, and
      a fastener having a proximal portion including spaced apart walls that define an implant cavity and a distal portion that extends through the axial opening and the transverse passageway such that the proximal portion sits above the proximal end of the shaft;
   connecting the distal end with tissue;
   rotating the distal portion relative to the proximal end for alignment with the transverse passageway and passage through the axial opening; and
   disposing the distal portion through the axial opening to connect the distal portion with tissue such that the distal end is disposed in spaced apart relation to the distal portion of the fastener.

18. A method as recited in claim 17, wherein the step of providing a bone fixation element comprises the proximal end including a plate that defines the axial opening, the plate having a first surface configured to engage tissue and a second surface engaging the proximal portion, the first surface including at least one bone penetrating element extending therefrom; and
   further comprising the step of engaging the at least one bone penetrating element with tissue after connecting the distal end with tissue.

19. A method as recited in claim 17, wherein the step of providing a bone fixation element comprises the proximal end including an inner threaded surface that defines the transverse passageway, the distal portion including a first portion, an intermediate portion and a second portion, the first portion of the distal portion being threaded for engagement with the inner threaded surface; and
   further comprising the step of engaging the first portion with the inner threaded surface after disposing the distal portion through the axial opening.

20. A bone fixation element comprising:
   a fastener including a proximal portion including spaced apart walls that define an implant cavity and a distal portion configured to penetrate tissue, the distal portion including a threaded first portion, a smooth intermediate portion and a second portion;
   a distal end comprising a shaft defining a straight longitudinal axis, the shaft comprising a proximal end having an axial opening and an opposite threaded end configured to penetrate tissue, the axial opening and the threaded end being coaxial with the longitudinal axis, the shaft comprising a transverse passageway that extends through a side surface of the shaft, the proximal end including an inner threaded surface and a plate that defines the axial opening, the transverse passageway being configured to guide the distal portion of the fastener into tissue along a selected trajectory, the transverse passageway defining a first axis disposed at an angular orientation of 30 degrees relative to the longitudinal axis, the inner threaded surface being configured for engagement with the first portion of the fastener,
   the plate having a first surface configured to engage tissue and a planar second surface disposed adjacent the proximal portion of the fastener, the first surface including a plurality of spikes extending therefrom and being disposed radially about the first surface;
   wherein the distal portion of the fastener is disposed with the transverse passageway such that the proximal portion sits above the proximal end of the shaft, the distal portion of the fastener being configured to penetrate tissue, the distal portion of the fastener being rotatable through 360° in a plurality of planes for alignment with the transverse passageway and passage through the axial opening such that the distal end is disposable in spaced apart relation to the distal portion of the fastener within tissue.

* * * * *

UNITED STATES PATENT AND TRADEMARK OFFICE
CERTIFICATE OF CORRECTION

PATENT NO. : 9,918,763 B2
APPLICATION NO. : 14/808077
DATED : March 20, 2018
INVENTOR(S) : Hynes et al.

Page 1 of 1

It is certified that error appears in the above-identified patent and that said Letters Patent is hereby corrected as shown below:

In the Specification

In Column 4, Line 1, delete "rumor" and insert -- tumor --, therefor.

In Column 10, Line 54, delete "axis at" and insert -- axis a1. --, therefor.

In the Claims

In Column 12, Line 21, in Claim 5, delete "relative In" and insert -- relative to --, therefor.

Signed and Sealed this
Seventh Day of August, 2018

Andrei Iancu
*Director of the United States Patent and Trademark Office*